United States Patent [19]

Orths et al.

[11] 4,355,907

[45] Oct. 26, 1982

[54] APPARATUS FOR PICKING UP A MOLTEN TEST SAMPLE OF METAL OR METAL ALLOYS AND MEASURING THE COOLING CURVE OF SAID SAMPLE

[75] Inventors: Kurt Orths, Ratingen; Milan Lampic, Marburg; Peter Berger, Düsseldorf-Benrath; Jörg Müller, Düsseldorf-Wersten; Herbert Löblich, Hilden, all of Fed. Rep. of Germany

[73] Assignee: Verein zur Förderung der Giesserei-Industrie, Düsseldorf, Fed. Rep. of Germany

[21] Appl. No.: 168,451

[22] Filed: Jul. 10, 1980

[30] Foreign Application Priority Data

Jul. 21, 1979 [DE] Fed. Rep. of Germany ....... 2929693

[51] Int. Cl.³ ................................................ G01J 5/08
[52] U.S. Cl. ..................................... 374/26; 374/131; 374/139; 374/157
[58] Field of Search ................... 73/DIG. 9, 425.4 R, 73/355 R, 17 R

[56] References Cited

U.S. PATENT DOCUMENTS

| | | | |
|---|---|---|---|
| 3,452,598 | 7/1969 | Jones, Jr. | 73/355 R |
| 3,570,277 | 3/1971 | Dorr et al. | 73/355 R |
| 3,745,834 | 7/1973 | Veltze | 73/355 R |
| 3,748,908 | 7/1973 | Falk | 73/354 |

*Primary Examiner*—S. Clement Swisher
*Attorney, Agent, or Firm*—Kenyon & Kenyon

[57] ABSTRACT

In apparatus for picking up a test sample of molten metal or metal alloys and measuring the cooling curve of said sample, comprising a sample receptor and an optical conductor leading from the receptor to a transducer, the receptor is a small, open ended refractory tube having a cavity for receiving the molten sample arranged at the free extremity of a lance with the optical conductor contained within the lance and terminating at the cavity in said receptor and a barrier is disposed between the cavity and the optical conductor, the barrier consisting of a heat resistant, highly thermally conductive material of such quality as to cause the material of the melt sample which is picked up to adhere thereto.

10 Claims, 1 Drawing Figure

APPARATUS FOR PICKING UP A MOLTEN TEST SAMPLE OF METAL OR METAL ALLOYS AND MEASURING THE COOLING CURVE OF SAID SAMPLE

BACKGROUND OF THE INVENTION

This invention relates to metallurgy in general and more particularly to the making of temperature measurements in molten samples.

Temperature measurements of molten and solidifying metals and alloys, taken for the purpose of ascertaining instantaneous temperature, as well as for studying thermal transformation processes occurring during solidification and cooling, are normally obtained through the use of thermo-electrical or optical measuring techniques. For thermo-electrical measuring, a thermocouple, sheathed in a protective tube, is introduced into the melt. The optical measuring method when applied to ascertain instantaneous melt temperature is usually carried out without physical contact while studying thermal transformation processes (thermo analysis). To accomplish this, an optical conductor is brought close to the cavity of a casting mold built for that purpose. Such temperature measuring operations are carried out, on the one hand, in order to determine the temperature of a melt at any given moment, e.g. for controlling a melting process, and, on the other hand, to enable conclusions to be drawn in respect of the composition of the metal alloy, solidification or freezing phenomena and transformation of thermal change behavior.

Measuring by means of thermocouple elements has the basic disadvantage of "indication inertia." For this reason the measuring operation must be extended over a certain length of time required to surmount this inertia, i.e., the time required to heat up the protective tube and the thermocouple. In order to obtain a correct temperature reading it is vital that the thermocouple remain intact at least up to completion of any one single measuring process. That is to say, the protective sheathing tubes must be dimensioned accordingly. It is this factor which essentially determines the length of measuring time required. Where thermocouples are used for a thermal analysis of a metal alloy in a casting mold, the inherent disadvantage of indication inertia has the further adverse effect that, with low casting molds, certain thermal effects of conversion processes are frequently not indicated at all because they occur and even terminate before the thermo-couple and its sheathing tube have warmed up. On the other hand, if the sheathing tube or coating is scantily dimensioned, in order to prevent just this risk, thermocouples are liable to be destroyed before the measuring operation has been accomplished. Because of the inertia of the thermocouple the thermal analysis must be carried out at a comparatively slow cooling rate in order to achieve adequate accuracy.

The contactless optical temperature measuring method has the drawback that the exposed surface of the melt thus measured differs from the ideal state of the "black body." Radiation then no longer reflects the true temperature of the melt. This is aggravated by the fact that radiation intensity is modified by slag formation on the surface of the melt. It is true that these difficulties can be overcome, with the aid of what are known as color pyrometers, but this measuring process is laborious and time consuming while its accuracy depends on the visual perception of the person making the measurement. In the case of optical thermal analysis work, the problems have been solved by using reflective coated optical conductors, i.e., fiber optics, and taking them right up to the cavity of the test mold. The sample contained in the mold may be considered a "black body." Furthermore, this extremely low inertia method also permits thermal analysis at high cooling rates, i.e., very small test samples.

More frequently the essential disadvantage of existing measuring equipment for the thermal analysis of metals arises from the need to transfer the molten metal alloy from the melting vessel to the test mold in order to carry out the thermal analysis, because this transfer involves loss of temperature, which detracts from the accuracy of the results, even where the virtually inertia free optical thermal analysis method is applied.

In a known arrangement, the receptor for the test sample is a casting mold having a capacity of slightly less than 50 cm$_3$. The molten metal is drawn from the melt and poured into the receptor. During this period of being drawn from the melt and introduced into the receptor the sample will already cool down so that potentially important cooling curve data cannot be ascertained. For this reason alone the range of application of this existing apparatus is somewhat restricted. Moreover, it is rather difficult and complicated to take metal from the melt by means of a suitable appliance and introduce it into the small mold.

It is, thus, the object of the present invention to expand the range of application of the type of equipment just described.

SUMMARY OF THE INVENTION

The present invention includes apparatus, of the general type described above, for picking up a molten test sample of metal or metal alloys and measuring the cooling curve of said sample, which consists of a sample receptor and a optical conductor line leading from said receptor to a data transducer.

According to the present invention, in order to achieve its object of expanded range, the receptor is a small open-ended refractory tube arranged at the free extremity of a lance which carries the optical conductor. Between the cavity in the tube wherein the molten test sample is received and the optical conductor there is arranged a barrier, e.g., platelet, a membrane, a vapor-deposited coating or the like consisting of a heat resistant and highly thermally conductive material of such quality as to cause the material of the molten test sample which has been picked up to adhere thereto.

The apparatus according to the present invention permits, in the simplest possible way, picking up the desired test sample directly from the melt and immediately measuring its cooling curve. Thus there is no longer any loss whatsoever of temperature data.

According to one embodiment of the present invention the platelet or like part consists of a substance which influences the texture of the test sample. For example, for cast iron, particularly with laminary graphite, the presentation of cooling curve data can be improved by a graphite platelet.

Suitable materials for the platelet or like part include graphite, preferably pyrographite, high-melting point oxides or silicates, e.g. zirconium oxide or zirconium silicate.

The platelet which is designed to protect the optical conductor, must transmit the temperature from the test sample to the optical conductor with an absolute minimum of time lag. For this reason it should be as thin as possible. A thickness of less than 0.5 mm, and in particular of 0.1 mm was found suitable for a graphite platelet.

The refractory material for the little tube may be a metal, a ceramic material, refactory glass or a sintered material. The tube must be resistant to temperatures above the melting point of the molten metal or metal alloy, that is to say generally above 1,500° C.

In order to make it easier for the molten metal to enter into the tube the latter may be provided with a vent hole.

If a platelet is used this may be clamped or wedged in the tube and, in particular, rest on a wall constriction of the latter.

Since the cooling curve is effectively measured right from the moment of pick-up, a very small quantity of molten metal/alloy is needed for the test sample. The receptor cavity may have a capacity of, for example, 1 to 2 g of molten metal.

BRIEF DESCRIPTION OF THE DRAWING

The single FIGURE is a representation of one embodiment of the measuring apparatus of the present invention.

DETAILED DESCRIPTION OF THE INVENTION

Figure 1:
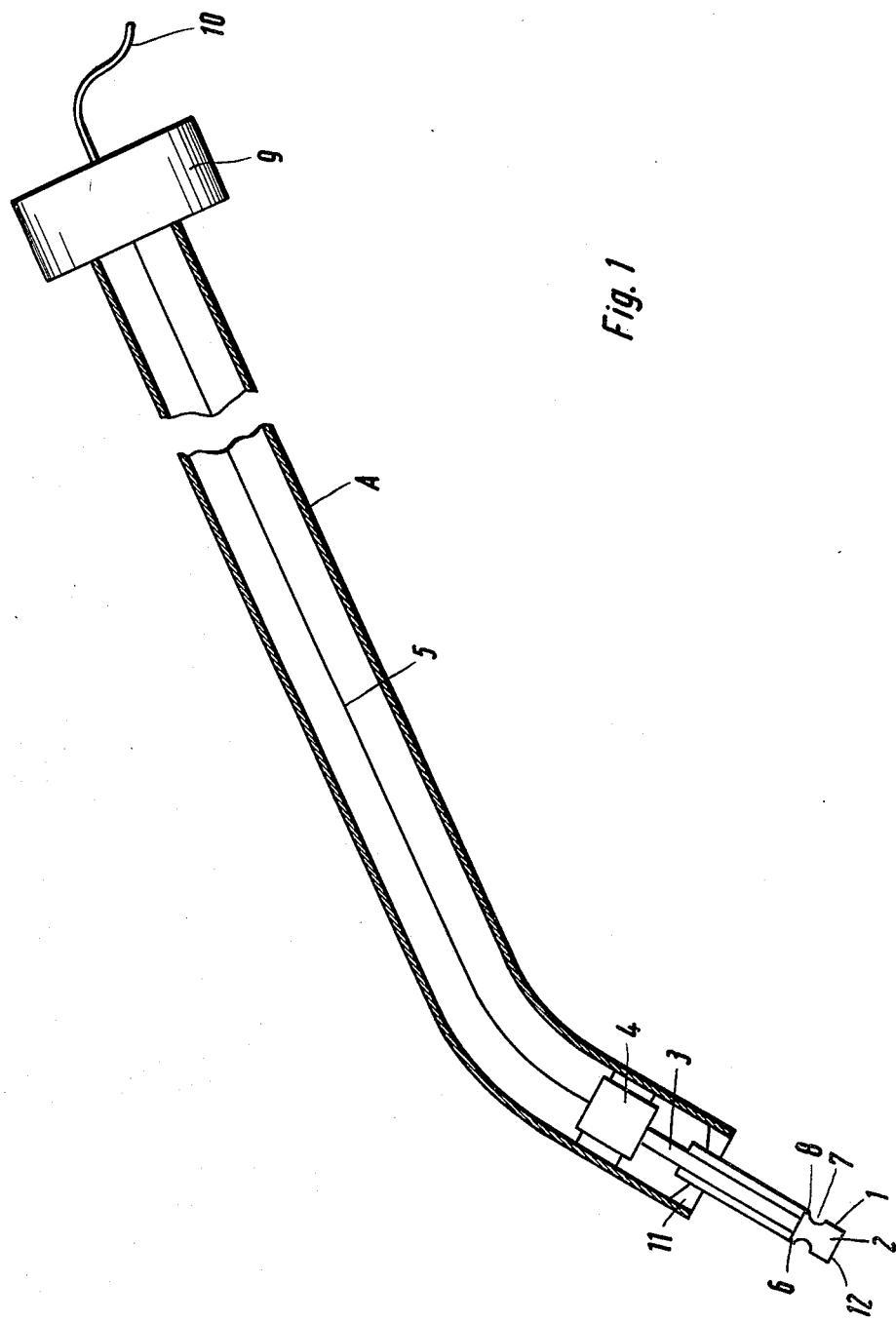

A small tube 1 of quartz glass is arranged at the free extremity of a lance A. Tube 1 provides a cavity 2 adapted to receive a molten test sample weighing between 1 and 2 g. The tube walls are pinched together to form a constriction 7 on which a graphite platelet 6 is supported. A rigid end part 3 of an otherwise flexible optical conductor 5 is arranged so that its frontal face comes up to the backside of platelet 6. This rigid end part 3 is retained by a holder 4 in the lance A. The other end of the flexible optical conductor 5 leads to an infrared detector 9 which converts the light signals into electric signals which are then transmitted via a cable 10 to a measuring instrument.

The tube 1 is retained at the outlet orifice of lance A by a collet 11 so that it can be readily exchanged. To protect it against slag and other impurities the open bottom of the tube 1 may be provided with an initial covering 12 which opens only after coming into contact with the melt. In the upper region of the cavity 2 the tube 1 has a vent hole 8.

The test sample is picked up by plunging the lance A with the little tube 1 into the melt so that the melt enters the tube 1 and rises up to platelet 6 where it sticks because of the special property of the platelet. The lance A is then pulled out and the cooling curve data can be registered immediately from that moment onward.

The advantages resulting from the present invention are substantially as follows:

(a) Temperature measuring of metal melts combined with simultaneous pick up of test sample for thermal analysis which is virtually free of inertia or time lag.

(b) Thermal analysis without risk of data falsification arising from insufficiently high sample pick up temperature.

(c) Optional variation of different structural states in test sample, i.e., receptor content, by application of cooling or heat absorbing chemo-metallurgically active liners.

(d) Long service life of the optical conductor without impairing measuring accuracy because of the protective barrier in front of the end face of the optical conductor.

(e) The receptor content can be easily picked up from the melt.

(f) The electric cable reaching right up to the lance affords great flexibility in the picking up of samples.

What is claimed is:

1. In apparatus for picking up a test sample of molten metal or metal alloys and measuring the cooling curve of said sample, comprising a sample receptor and a optical conductor leading from the receptor to a transducer, the improvement comprising:
   (a) a lance;
   (b) the receptor being a small, open ended refractory tube having a cavity for receiving the molten sample arranged at the free extremity of said lance;
   (c) the optical conductor contained within said lance and terminating at said cavity in said receptor;
   (d) a barrier disposed between said cavity and said optical conductor, said barrier consisting of a heat resistant, highly thermally conductive material of such quality as to cause the material of the melt sample which is picked up to adhere thereto.

2. The improvement according to claim 1, wherein said barrier consists of a substance which influences the texture of the test sample.

3. The improvement according to claim 1 wherein said barrier is selected from the group consisting of graphite, preferably pyrographite, high-melting oxides and silicates such as zirconium oxide, or zirconium silicate.

4. The improvement according to claim 1 wherein said barrier is less than 0.5 mm thick.

5. The improvement according to claim 4 wherein said barrier is less than 0.1 mm thick.

6. The improvement according to claim 1 wherein said refractory tube is made of a material selected from the group consisting of metal, ceramics, refactory glass and a sintered material.

7. The improvement according to claim 1 and further including a vent hole in said refractory tube.

8. The improvement according to claim 1 wherein said barrier comprises a platelet clamped in said tube.

9. The improvement according to claim 7 wherein said platelet rests on a constricted wall region of said tube.

10. The improvement according to claim 1 wherein said cavity has a capacity for holding from 1 to 2 g of molten metal or metal alloy.

* * * * *